United States Patent [19]
Cassels

[11] Patent Number: 5,914,114
[45] Date of Patent: Jun. 22, 1999

[54] **METHOD OF RAISING ANTIBODIES AGAINST *E. COLI* OF THE FAMILY CS4-CFA/I**

[75] Inventor: Frederick J. Cassels, Ellicott City, Md.

[73] Assignee: The United States of America as represented by the Secretary of the Army, Washington, D.C.

[21] Appl. No.: 08/460,617

[22] Filed: Jun. 2, 1995

[51] Int. Cl.$^6$ ............... A61K 39/108; A61K 39/00; A61K 38/00; C07K 2/00
[52] U.S. Cl. ............... 424/241.1; 424/184.1; 424/194.1; 424/234.1; 424/242.1; 424/169.1; 424/257.1; 424/185.1; 530/300; 530/333; 530/324; 514/12; 514/62; 514/2; 514/867
[58] Field of Search ............... 424/241.1, 184.1, 424/194.1, 234.1, 242.1, 169.1, 257.1, 185.1; 530/300, 333, 324; 514/12, 62, 2, 867

[56] References Cited

U.S. PATENT DOCUMENTS

| | | |
|---|---|---|
| 4,411,888 | 10/1983 | Klipstein . |
| 4,971,794 | 11/1990 | Linggood et al. . |
| 5,017,372 | 5/1991 | Hastings . |
| 5,071,977 | 12/1991 | Cassels et al. . |
| 5,190,746 | 3/1993 | Cassels et al. . |
| 5,208,024 | 5/1993 | Van Den Bosch . |
| 5,417,986 | 5/1995 | Reid et al. . |
| 5,593,679 | 1/1997 | Van Den Bosch . |
| 5,627,163 | 5/1997 | Heerze et al. . |
| 5,637,576 | 6/1997 | Heerze et al. . |
| 5,698,416 | 12/1997 | Wolf et al. . |

FOREIGN PATENT DOCUMENTS 9201703  2/1992  WIPO .

OTHER PUBLICATIONS

Wennerås et al Infect & Immun. 63/2: 640–646, 1995.
Yakhchali et al Behring Inst. Mitt. 98: 124–134, 1997.
Clark et al Inf & Imm. 60/3: 1254–1257, 1992.
Cassels et al. J. Indus. Microbiol. 15:214–226 1995.
Hall et al. J. Bacteriol. 1989 171(11):6372–74.
Grewal et al. Vacccine. 1993 11(2):221–226.
Caron et al. 1989 PNAS. 86:963–967.
Sommerfelt et al. 1992. Inf–Imm. 60(9):3799–3806.
McConnell et al. 1989. Fems. Microbiol Lett, 61:105–108.
Smyth et al. 1991. Microbial Surface Comp. & Toxins in Relation to Pathogenesis. Ed. Ron et a pp. 37–53.
Cassels. et al. Inf & Inm. 1992 60(6):2174–81.
Tacket et al. 1987. Inf & Imm. 55(5):1063–69.
Karjalainen et al. 1989. Inf & Imm. 57(4):1126–130.
Rudin. et al. 1994 Inf & Imm. 62(10):4339–46.

*Primary Examiner*—Nita Minnifield
*Attorney, Agent, or Firm*—Charles H. Harris; John Francis Moran

[57] ABSTRACT

A consensus poptide of 36 amino acids has been designed which acts as an immunogen raising antibodies against the proteins of all members of the *E. coli* family CS4-CFA/1. While the N-terminus of members of this family of organisms shows a high degree of identity, the remainder of the sequence of the proteins shows much less homology across the strains. The region of the protein represented in the subunit encompasses known linear B- and T-cell epitopes of CFA/I. The consensus peptide has a high level of homology to strains bearing six different colonization factors. The consensus peptide is of the formula:

VEKNITVTASVDPTIDLLQADGSALPSAVALTYSPA

An alternative peptide, identified as consensus peptide 2 is of the formula:

VEKNITVTASVDPTIDLLQADGSALPASVALTYSPA

9 Claims, No Drawings

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 25 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
              (A) ORGANISM: E coli (xi) SEQUENCE DESCRIPTION: SEQ ID NO:1:

Val Glu Lys Asn Ile Thr Val Thr Ala Ser Val Asp Pro Thr Ile Asp
1               5                  10                  15

Ile Leu Gln Ala Asn Gly Ser Ala Leu
            20                  25

(2) INFORMATION FOR SEQ ID NO:2:

(i) SEQUENCE CHARACTERISTICS:
              (A) LENGTH: 36 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
              (A) ORGANISM: E coli (xi) SEQUENCE DESCRIPTION: SEQ ID NO:2:

Val Glu Lys Asn Ile Thr Val Thr Ala Ser Val Asp Pro Thr Ile Asp
1               5                  10                  15

Leu Leu Gln Ala Asp Gly Ser Ala Leu Pro Ala Ser Val Ala Leu Thr
            20                  25                  30

Tyr Ser Pro Ala
        35

(2) INFORMATION FOR SEQ ID NO:3:

(i) SEQUENCE CHARACTERISTICS:
              (A) LENGTH: 37 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
              (A) ORGANISM: E coli (xi) SEQUENCE DESCRIPTION: SEQ ID NO:3:

Cys Val Glu Lys Asn Ile Thr Val Thr Ala Ser Val Asp Pro Thr Ile
1               5                  10                  15

Asp Leu Leu Gln Ala Asp Gly Ser Ala Leu Pro Ser Ala Val Ala Leu
            20                  25                  30

Thr Tyr Ser Pro Ala
        35

(2) INFORMATION FOR SEQ ID NO:4:

(i) SEQUENCE CHARACTERISTICS:
             (A) LENGTH: 37 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
             (A) ORGANISM: E coli (xi) SEQUENCE DESCRIPTION: SEQ ID NO:4:

Val Glu Lys Asn Ile Thr Val Thr Ala Ser Val Asp Pro Val Ile Asp
1               5                   10                  15

Leu Leu Gln Ala Asp Gly Ser Ala Leu Pro Ser Ala Val Ala Leu Thr
            20                  25                  30

Tyr Ser Pro Ala Ser
        35

(2) INFORMATION FOR SEQ ID NO:5:

(i) SEQUENCE CHARACTERISTICS:
             (A) LENGTH: 37 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
             (A) ORGANISM: E coli (xi) SEQUENCE DESCRIPTION: SEQ ID NO:5:

Val Glu Lys Thr Ile Ser Val Thr Ala Ser Val Asp Pro Thr Val Asp
1               5                   10                  15

Leu Leu Gln Ser Asp Gly Ser Ala Leu Pro Asn Ser Val Ala Leu Thr
            20                  25                  30

Tyr Ser Pro Ala Val
        35

(2) INFORMATION FOR SEQ ID NO:6:

(i) SEQUENCE CHARACTERISTICS:
             (A) LENGTH: 37 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
             (A) ORGANISM: E coli (xi) SEQUENCE DESCRIPTION: SEQ ID NO:6:

Val Glu Lys Asn Ile Thr Val Thr Ala Ser Val Asp Pro Thr Ile Asp
1               5                   10                  15

Ile Leu Gln Ala Asp Gly Ser Tyr Leu Pro Thr Ala Val Glu Leu Thr
                20                  25                  30

Tyr Ser Pro Ala Ala
        35

(2) INFORMATION FOR SEQ ID NO:7:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: E coli (xi) SEQUENCE DESCRIPTION: SEQ ID NO:7:

Val Glu Lys Asn Ile Thr Val Arg Ala Ser Val Asp Lys Leu Ile Asp
1               5                   10                  15

Leu Leu Gln Ala Asp Gly Thr Ser Leu Pro Asp Ser Ile Ala Leu Thr
                20                  25                  30

Tyr Ser Val Ala
        35

(2) INFORMATION FOR SEQ ID NO:8:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: E coli (xi) SEQUENCE DESCRIPTION: SEQ ID NO:8:

Val Glu Lys Asn Ile Thr Val Thr Ala Ser Val Asp Pro Thr Ile Asp
1               5                   10                  15

Ile Leu Gln Ala Asn Gly Ser Ala Leu
                20                  25

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide

```
    (iii) HYPOTHETICAL: NO (iv) ANTI-SENSE: NO (v) FRAGMENT TYPE: N-terminal (vi) ORIGINAL SOURCE:
          (A) ORGANISM: E coli (xi) SEQUENCE DESCRIPTION: SEQ ID NO:9:

Ala Glu Ile Asn Ile Thr Val Thr Ala Ser Val Asp Pro Val Ile Asp
1               5                   10                  15

Leu Leu Gln Ala
            20
```

METHOD OF RAISING ANTIBODIES AGAINST *E. COLI* OF THE FAMILY CS4-CFA/I

FIELD OF THE INVENTION

This invention provides means of immunization of humans with a peptide or denatured protein against enterotoxigenic *E. coli* (ETEC) strains of the CS4-CFA/I family. The antibodies raised by the peptides and vaccines may be used as diagnostic agents to identify antigens of CS4-CFA/I bacteria.

BACKGROUND OF THE INVENTION

The effect of *E. coli* in mammals is dependent on the particular strain of organism. Many beneficial *E. coli* are present in the intestines. Since the initial association with diarrheal illness, five categories of diarrheagenic *E. coli* have been identified and are presently recognized: enterotoxigenic (ETEC), enteropathogenic (EPEC), enterohemorrhagic (EHEC), enteroaggregative (EAggEC), and enteroinvasive (EIEC). These categories are grouped according to characteristic virulence properties, such as elaboration of toxins and colonization factors and/or by specific types of interactions with intestinal epithelial cells. ETEC are the most common of the diarrheagenic *E. coli* and pose the greatest risk to travelers. *E. coli* of the family CS4-CFA/I are some of the more common enterotoxigenic *E. coli*. There is need for vaccines which are specific against this class of *E. coli* that give rise to antibodies that cross-react with and cross-protect against the more common members of the CS4-CFA/I family. There are six members of this family of ETEC fimbrial proteins, CFA/I, CS1, CS2, CS4, CS17 and PCF 0166. ETEC are responsible for high infant mortality in developing countries, with an estimate that almost 800,000 deaths per year due to these organisms. These organisms also cause illness in adult travelers to regions where the disease is endemic. No licensed vaccine exists against these organisms. The present vaccines being tested present problems related to manufacturing. So far, there has been no demonstration of significant efficacy of the prior art vaccines.

Colonization factor antigens (CFA) of ETEC are important in the initial step of colonization and adherence of the bacterium to intestinal epithelia. In epidemiological studies of adults and children with diarrhea, CFA/I is found in a large percentage of morbidity attributed to ETEC. The CFA/I is present on the surfaces of bacteria in the form of pili (fimbriae), which are rigid, 7 nm diameter protein fibers composed of repeating pilin subunits. The CFA/I antigens promote mannose-resistant attachment to human brush borders with an apparent sialic acid sensitivity. Hence, it has been postulated that a vaccine that establishes immunity against these proteins may prevent attachment to host tissues and subsequent disease.

Preferred that vaccines are those that give consistent protection and that are relatively inexpensive to manufacture. Immunization with a single antigen, either a peptide or individual denatured protein, that could simultaneously protect against organisms bearing this family of differing colonization factors is needed. Hence, it is desirable to identify peptides that do not rely on living organisms for production. Experimental evidence indicates that when animals are immunized with intact fimbriae, cross-reactivity is minimal.

Testing for CFA/I, CS1, CS2, CS3, CS4, CS5 and CS6 has been the most common diagnostic evaluation attempted. CFA/I, CS3 and CS6 may occur alone, but with rare exception CS1 is only found with CS3, CS2 with CS3, CS4 with CS6 and CS5 with CS6. These colonization factor-bearing (CF) organisms have been reported to account for up to 75% or as little as 23% of the ETEC, depending on location of the study.

DETAILED DESCRIPTION OF THE INVENTION

A study of proteins in *E. coli* belonging to the CS4-CFA/I family resulted in the finding that the N-terminal region of the protein maintains a high degree of sequence identity between members of this group. Immunological evidence shows that cross-reaction exists between members of the family CS4-CFA/1. Two problems of significant magnitude exist in the vaccine field that relate to immunization against varying strains of organisms: 1) is it possible to immunize against several strains using a single antigen, whether a protein or a peptide, and 2) will antibodies raised against peptides or denatured proteins be effective against proteins having tertiary structures due to folding and disulfide bonding and to quaternary structures having not only tertiary structure, but also strong interaction between protein units? *E. coli* of the CS4-CFA/1 family have fimbriae on the surface of the cell which are composed of quaternary proteins composed of repeating protein units. Previously published experimental evidence indicates that when animals are immunized with intact fimbriae, cross-reactivity is minimal. However, when fimbriae are dissociated into subunits, i.e., the quaternary structure was broken down, response to linear epitopes occurs. The strain-specific antigens used in the examples were denatured protein subunits of the fimbriae.

A consensus peptide of 36 amino acids has been designed which raises acts as an immunogen raising antibodies against the proteins of all members of the *E. coli* family CS4-CFA/1. While the N-terminus of members of this family of organisms shows a high degree of identity, the remainder of the sequence of the proteins shows much less homology across the strains.

The region of the protein represented in the subunit encompasses known linear B- and T-cell epitopes of CFA/I. The consensus peptide has a high level of homology to strains bearing six different colonization factors. The consensus peptide is of the formula:

VEKNITVTASVDPTIDLLQADGSALPSAVALTYSPA Seq. ID No. 3

An alternative peptide, identified as consensus peptide 2 of the formula:

VEKNITVTASVDPTIDLLQADGSALPASVALTYSPA Seq. ID No. 2 is made in the same manner as described in Example 1. The consensus peptide was constructed based on the analogous peptides from CFA/I, CS1, CS2, CS4, CS17 and PCF 0166. The consensus peptide was shown to raise antibodies which agglutinated whole bacteria bearing colonization factors CFA/I, CS2, and CS1. The serum samples from animals that had been immunized with the denatured protein from strains 0166, CFA/I, and CS2 were tested. Since the antibodies recognized the 0166 strain but did not cause agglutination of the organisms,; it is clear that reactivity is not always evidenced by agglutination.

The analogous peptides of the denatured protein subunits from the various strains contain the following sequences:
CFA/1 VEKNITVTASVDPVIDLLQADGSALP-
SAVALTYSPAS Seq. ID No. 4

CS1 VEKTISVTASVDPTVDLLQSDGSALPNS-
VALTYSPAV Seq. ID No. 5
CS4 VEKNITVTASVDPTID-
ILQADGSYLPTAVELTYSPAA Seq. ID No. 6
CS17 VEKNITVRASVDKLIDLLQADGTSLPd-
SIALTYSVA Seq. ID No. 7
PCF0166 VEKNITVTASVDPTIDILQANGSAL Seq. ID No. 8
CS2 AEINITVTASVDPVIDLLQA Seq. ID No. 9

As indicated in the data provided herein, many of the denatured proteins gave rise to antibodies that are reactive with proteins of other strains as evidenced by precipitation studies on nitrocellulose and that are reactive with surface antigens of the fimbriae as evidence by agglutination of organisms.

Peptides or denatured proteins of the invention may be conjugated to other moieties such as other proteins, peptides, hydrophobic moieties and proteosomes. The peptides, whether free or conjugated, may be administered by mouth in protected form. The peptides may thereby be presented to the mucosa of the intestinal tract to raise mucosal immune response. For example, the peptides may be protected by encapsulation in accord with the teachings of U.S. Pat. No. 5,417,986, which is incorporated herein by reference in its entirety. Peptides and denatured proteins may also be formulated in other protection means such as liposomes or microcrystals. The protected peptides or denatured proteins are particularly useful for administration by mouth.

Vaccine compositions may be introduced into the patient by conventional means, including parenteral routes (subcutaneous, intradermal, intramuscular) and by direct application to-mucous membranes. Lyophilized compositions may be "snorted" into the nasal cavity. Dosage will depend on the particular agent administered. The method of administration directly to the mucous membranes is exemplified herein. It should be understood that the use of this technology disclosed herein has particularly wide applications for making of immunogens for administration to the mucous membranes. The immunogenic compositions containing the peptides may contain adjuvants known in the art, such as Feund's adjuvant or alum.

Materials and Methods

Conlonization factors (CF) from ETEC strains of each member of the CFA/I family were purified and run on polyacrylamide gels. Stained bands from transfers of the gels to PVDF membrane were excised and subjected to automated Edman degradation. Peptides were synthesized by solid phase automated Fmoc chemistry. The peptides were prepared by solid phase peptide synthesis using a 430A peptide synthesizer (applied Biosystems, Inc., Foster City, Calif.) using 9-fluorenylmethoxycarbonyl (Fmoc) amino and t-butyl side chain protecting groups supported by HMP resin (p-hydroxymethylphenoxymethyl polystyrene resin). All solvents and side chain protected amino acids were also obtained from Applied Biosystems and used in accord with the instruction provided therewith. Following synthesis, protecting groups were removed by acid hydrolysis using anisole and ethanedithiol as scavengers. Amino acid analysis and reverse-phase high pressure liquid chromatography were used to determine amino acid content and peptide purity respectively.

The consensus peptide was conjugated to bovine serum albumin (BSA) or tetanus toxoid. When the peptide was conjugated to as indicated below, a cysteine residue was added at the terminal end of the peptide to provide the following consensus peptide:

CVEKNITVTASVDPTIDLLQADGSALPSAVALTYSPA

The albumin or toxoid was then iodoacetylated. The peptide was mixed with the acetylated albumin or toxoid. (Sulfide bonds are thereby formed between cysteine residus providing a conjugated protein.) BSA-dexran is also appropriate for conjugation with these antigens.

Immunogenic compositions contained complete Freund's adjuvant and were administered to rabbits subcutaneously on day 1. On day 21, a booster shot was given. The booster shot differed from the first dosing in that a smaller amount of protein was given and the complete Freund's adjuvant was replaced with incomplete Freund's adjuvant. On day 32 the animals were bleed.

Example 1

Rabbits were bled, then immunized on day 0 with a composition containing 280 µg peptide/BSA conjugate in Freund's complete adjuvant. On day 21, the animals were boosted with 140 µg peptide/BSA conjugate in Freund's incomplete adjuvant. Blood was drawn on day 32. The interaction of antibodies raised against the specific antigens of the denatured proteins of the various strains was studied by comparing interaction of serum from the animals obtained on day 0 with interaction of serum from the animals obtained on day 32 by Western blot. In all instances, the Western blot was negative for reaction with serum obtained on day 0. The Western blot data on interaction of immune serum collected on day 32 with the denatured proteins is given below with 0 being no reaction and 4 being a strong reaction:

| Titer | 1:50 | 1:500 | 1:5000 | 1:50000 |
|-------|------|-------|--------|---------|
| CS1   | 4    | 4     | 4      | 4       |
| CS2   | 4    | 4     | 4      |         |
| CS4   | 4    | 4     | 3      | 2       |
| CS17  | 4    | 3     | 2      | 0.5     |
| 0166  | 4    | 1     | 3      |         |
| CFA/I | 4    | 3     | 2      |         |

Example 2

An immunogenic composition is prepared containing 280 µg/ml of a conjugate of a peptide of the formula:

VEKNITVTASVDPTIDLLQADGSALPSAVALTYSPA bound to BSA through a cysteine in complete Freund's reagent.

Example 3

A immunogenic composition is prepared containing 400 µg/ml of a peptide of the formula:

VEKNITVTASVDPTIDLLQADGSALPSAVALTYSPA in complete Freund's adjuvant.

Example 4

Rabbits were given a composition containing 400 µg peptide of the formula:

VEKNITVTASVDPTIDLLQADGSALPSAVALTYSPA in complete Freund's adjuvant.

The response was evaluated as in Example 2:

| Titer | 1:50 | 1:500 | 1:5000 | 1:50000 |
|-------|------|-------|--------|---------|
| CS1   | 4    | 4     | 2      | 1       |
| CS2   |      |       |        |         |
| CS4   | 2    | 0     | 0      | 0       |
| CS17  | 2    | 0     | 0      | 0       |
| 0166  | 4    | 2     |        |         |
| CFA/I |      |       |        |         |

Example 5

The same study was done comparing antibodies raised to denatured proteins of 0166.

| Titer | 1:1000 | 1:10000 | 1:100000 |
|-------|--------|---------|----------|
| CS1   | 3      | 0.5     | 0        |
| CS2   | 2      | 1       | 0        |
| CS4   | 2      | 0.5     | 0        |
| CS17  | 3      | 0.5     | 0        |
| 0166  | 4      | 3       | 1        |
| CFA/I | 3      | 0.5     | 0        |

Example 6

Effect of antibody raised to denatured protein was studied in the manner of example 5.

| Titer | 1:1000 | 1:10000 | 1:100000 |
|-------|--------|---------|----------|
| CS1   | 4      | 3       | 0.5      |
| CS2   | 4      | 2       | 0        |
| CS4   | 3      | 1       | 0        |
| CS17  | 3      | 1       | 0.5      |
| 0166  | 4      | 1       | 0        |
| CFA/I | 3      | 0       | 0        |

Example 7

Studies were conducted to determine whether antibodies raised to the peptide would cause agglutination of whole bacteria of various strains. Antibody to three consensus peptide antigen preparations were compared: 1) peptide conjugated to bovine serum albumin (aPepBS), 2) free peptide (PepFr) and 3) peptide conjugated to tetanus toxoid (PepTT). The tetanus toxoid was conjugated to the peptide using the described above for conjugation to BSA. The three preparations were used to immunize two animals each. The serum was then contacted with whole bacteria and the slides were inspected for agglutination of the bacteria.

| CF    | aPepBSA | aPepFr | aPepTT |
|-------|---------|--------|--------|
| CS1   | 1/2     | 0/2    | 1/2    |
| CS2   | 2/2     | 0/2    | 2/2    |
| CS4   | 0/2     | 0/2    | 0/2    |
| CS17  | 0/2     | 0/2    | 0/2    |
| 0166  | 0/2     | 0/2    | 0/2    |
| CFA/I | 1/2     | 0/2    | 2/2    |

In view of the test data, it is seen that the data indicates that consensus proteins can give rise to antibodies that are reactive with denatured proteins of species of the family CF4-CFA/1 and that such antibodies also cause agglutination of organisms of more than one strain of E. coli of the CF4-CFA/1 family. However, it is also seen that conjugation to a larger molecule provides improved properties to the peptides for purposes of raising antibodies to the whole bacteria and the proteins of these organisms.

The preparation of analogous peptides of the various strains of this family of organisms containing the sequences disclosed above may also be used as vaccine cocktails. The peptides could be prepared by the methods disclosed herein or by other methods of peptide synthesis known in the art. The denatured proteins themselves may be used as antigens for preparation of vaccines in order to raise antibodies against E. coli of the family CFA/I. The analogous peptides or denatured proteins could be conjugated to proteins in accord with the methods taught herein. Hence, the instant invention also relates to vaccine compositions containing at least one denatured protein from an E. coli of the family CFA/I in a pharmaceutically acceptable carrier which may contain an adjuvant. The denatured fimbrial protein or any of the peptides disclosed herein may be conjugated to molecules which enhance antigenicity and administered as vaccines.

Additional peptides for use in accord with the teachings herein can also be designed based on the amino acid sequences disclosed herein for use in vaccines. A peptide of at least 30 residues would be preferred. The antigenicity of the smaller peptides would be enhanced by conjugation to larger molecules known in the art to increase antigenicity.

I claim:

1. A concensus peptide containing the sequence:
VEKNITVTASVDPTIDLLQADGSALPSAVALTYSPA, Seq. ID No. 3 or
VEKNITVTASVDPTIDLLOADGSALPASVALTYSPA, Seq. ID No. 2.

2. The peptide of claim 1 conjugated to a molecule which increases antigenicity.

3. The peptide of claim 1 conjugated to albumin.

4. A composition comprising a peptide of claim 1 in a pharmaceutically acceptable carrier.

5. The composition of claim 4 containing, additionally, an adjuvant.

6. A composition comprising at least one denatured fimbrial protein from an *E. coli* of the family CS4-CFA/I in a pharmaceutically acceptable carrier.

7. The composition of claim 4 wherein the peptide is conjugated to a molecule which enhances antigenicity.

8. The composition of claim 7 wherein the molecule which enhances antigenicity to which the peptide is conjugated is tetanus toxoid.

9. A method of immunizing a mammal against disease caused by *E. coli* of the family CS4-CFA/I comprising administration of an immunogenic effective amount of the composition of claim 4.

* * * * *